United States Patent
Recht et al.

(10) Patent No.: US 9,594,039 B2
(45) Date of Patent: Mar. 14, 2017

(54) PHOTOMETRIC ENTHALPY CHANGE DETECTION SYSTEM AND METHOD

(71) Applicant: Palo Alto Research Center Incorporated, Palo Alto, CA (US)

(72) Inventors: Michael I. Recht, San Carlos, CA (US); Joerg Martini, San Francisco, CA (US); Gregory L. Whiting, Menlo Park, CA (US); Francisco E. Torres, San Jose, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 147 days.

(21) Appl. No.: 14/583,239

(22) Filed: Dec. 26, 2014

(65) Prior Publication Data
US 2016/0187273 A1 Jun. 30, 2016

(51) Int. Cl.
*G01N 25/20* (2006.01)
*G01N 25/48* (2006.01)
*G01N 21/00* (2006.01)

(52) U.S. Cl.
CPC .......... *G01N 25/482* (2013.01); *G01N 25/20* (2013.01); *G01N 21/00* (2013.01)

(58) Field of Classification Search
CPC .. G01N 25/482; G01N 33/68; G01N 33/6803; G01N 25/20; G01N 21/00; Y10T 436/2575
USPC ... 436/501, 536, 86, 94, 147, 164, 165, 180; 422/51, 82.05, 82.09, 502, 503; 435/6.1, 435/7.1, 287.1, 287.2, 287.3, 288.7; 506/7, 9, 11, 39
See application file for complete search history.

(56) References Cited

U.S. PATENT DOCUMENTS

| | | | |
|---|---|---|---|
| 7,419,835 B2* | 9/2008 | Torres | G01N 25/4846 374/31 |
| 7,521,253 B2* | 4/2009 | Bruce | B82Y 15/00 436/147 |
| 2011/0263464 A1* | 10/2011 | De Bruyker | B01F 13/0071 506/40 |
| 2015/0079583 A1* | 3/2015 | Baudenbacher | B01L 3/502784 435/5 |

OTHER PUBLICATIONS

De Bruyker et al. Lab on a Chip, vol. 11, 2011, pp. 3313-3319.*
Ross et al., Temperature Measurement in Microfluidic Systems Using a Temperature-Dependent Fluorescent Dye, Analytical Chemistry, Sep. 1, 2001, pp. 4417-4123, vol. 73, No. 17, Published on Web Jul. 24, 2001.

(Continued)

*Primary Examiner* — Maureen Wallenhorst
(74) *Attorney, Agent, or Firm* — Fay Sharpe LLP

(57) ABSTRACT

A method for detecting an enthalpy change includes providing a first mixture and a second mixture to a drop generator. The first mixture includes a ligand. The second mixture contains a target molecule. The method further includes generating a drop in the drop generator. The drop includes the target molecule, a temperature-sensitive reporter compound, and the ligand. The method also includes measuring a property of the temperature-sensitive reporter compound in the drop to determine an amount of enthalpy change that has occurred.

20 Claims, 3 Drawing Sheets

(56) References Cited

OTHER PUBLICATIONS

Parasassi et al., Laurdan and Prodan as Polarity-Sensitive Fluorescent Membrane Probes, Journal of Fluorescence, pp. 365-373, vol. 8, No. 4, 1998 Plenum Publishing Company.
Miller et al., High-resolution dose-response screening using droplet-based microfluidics, PNAS, Jan. 10, 2012, pp. 378-383, vol. 109, No. 2, www.pnas.org/cgi/doi/10.1073/pnas.1113324109.
Shim et al., Ultrarapid Generation of Femtoliter Microfluidic Droplets for Single-Molecule-Counting Immunoassays, American Chemical Society, 2013, pp. 5955-5964, vol. 7, No. 7, Published online Jun. 27, 2013, 10.1021/nn401661d.
Shiraishi et al., A Hemicyanine-Conjugated Copolymer as a Highly Sensitive Fluorescent Thermometer, American Chemical Society, 2008, pp. 4273-4279, Published on Web Mar. 4, 2008.I.
Kiesel et al., Wavelength Monitors for Optical Sensing Applications, www.photonics.com, Mar. 2007, pp. 1-6.
McLaurin et al., Dual-Emitting Nanoscale Temperature Sensors, Chemistry of Materials, American Chemical Society, 2013, pp. 1283-1292, ACS Publications.
Gota et al., Temperature-Dependent Fluorescence Lifetime of a Fluorescent Polymeric Thermometer, Poly($N$-isopropylacrylamide), Labeled by Polarity and Hydrogen Bonding Sensitive 4-Sulfamoyl-7-aminobenzofurazan, American Chemical Society 2008, pp. 2829-2836, J. Phys. Chem B 2008, 112, Published on Web Feb. 16, 2008.
Guo et al., Droplet microfluidics for high-throughput biological assays, The Royal Society of Chemistry, Lab on a Chip, 2012, 10 pages, DOI: 10.1039/c21c21147e, www.rsc.org/loc.
Hoang et al., Dynamic temperature measurement in microfluidic devices using thermochromics liquid crystals, The Royal Society of Chemistry 2008, pp. 484-487. Lab Chip, 2008, www.rsc.org/loc.
Sjostrom et al., High-throughput screening for industrial enzyme production hosts by droplet microfluidics, The Royal Society of Chemistry 2014, pp. 806-813. Lab Chip, 2014, 14, www.rsc.org/loc.
Ennulat et al., The Selective Light Reflection by Plane Textures, Molecular Crystals and Liquid Crystals, 13:4, 1971, pp. 337-355, http://dx.doi.org/10.1080/15421407108083550. Publisher: Taylor & Francis, published online: Mar. 28, 2007.
Dolomite, 2 Reagent Droplet Chips, product datasheet, pp. 1-10, The Dolomite Centre Ltd., MAR-000058 v1.4, date unknown.
Dabri, Digital particle image thermometry/velocimetry: a review, Exp Fluids (2009), 46: pp. 191-241, Springer.
Baret et al., Fluorescence-activated droplet sorting (FADS): efficient microfluidic cell sorting based on enzymatic activity, Lab on a Chip, vol. 9, No. 13, 7 Jul. 2009, pp. 1817-1972, RSC Publishing, www.rsc.org/loc.
Agresti et al., Ultrahigh-throughput screening in drop-based microfluids for directed evolution, 2009, PNAS Mar. 2010, vol. 107, No. 9, pp. 4004-4009, www.pnas.org/cgi/doi/10.1073/pnas.0910781107.
Engineering, Corrections and Editorial Expression of Concern, PNAS, Apr. 6, 2010, vol. 107, No. 14, pp. 6550-6551, www.pnas.org.
Abbyad et al., Dynamic Stokes shift in green fluorescent protein variants, PNAS, Dec. 18, 2007, vol. 104, No. 51, pp. 50189-20194, www.pnas.org/cgi/doi/10/1073/pnas.0706185104.

\* cited by examiner

PHOTOMETRIC ENTHALPY CHANGE DETECTION SYSTEM AND METHOD

BACKGROUND

This disclosure relates generally to an apparatus and method for an improved calorimeter, and more specifically, to a system and method for an improved calorimeter for measuring the heat released or absorbed during chemical reactions.

Screening campaigns, including high-throughput screening (HTS) campaigns, typically rely on assays using library compounds (e.g., labeled ligands or enzyme substrates. Artifacts associated with labeling have led to erroneous identification of active compounds.

HTS campaigns have historically relied on binding assays using labeled (fluorescent, radioactive) reporter constructs or enzymatic assays using labeled substrates. The attachment of fluorescent tags or development of fluorescent substrates requires additional assay development work and these modifications of the ligand or substrate can sometimes have adverse effects on binding/catalysis, leading to false positives and false negatives.

Calorimetry is the measurement of the quantity of heat evolved or absorbed in various processes (e.g., chemical reactions, changes of state, and formation of solutions). Calorimetry is a powerful technique for characterizing biochemical interactions, including enzymatic reactions, ligand binding, and organelle and cellular activity. It does not require labeling or immobilization of reagents. However, conventional calorimeters are limited by large sample requirements and low throughput. Accordingly, the use of calorimetry is relegated to a limited number of high-value measurements.

It would be desirable to develop new systems and methods for screening active compounds that utilize smaller samples, permit greater throughput, and avoid the problems associated with labeling.

BRIEF DESCRIPTION

An enthalpy change detection method includes providing a first mixture containing one or more library compounds (ligands) to a drop generator; providing a second mixture containing a target molecule to the drop generator; generating a drop in the drop generator, the drop containing the target molecule, a temperature-sensitive reporter compound, and a single molecule (or one concentration) of one library compound (ligand); and measuring an electromagnetic property of the temperature-sensitive reporter compound in the drop to determine whether the enthalpy change has occurred. The electromagnetic property may be an optical property, for example absorption, absorption spectrum, fluorescence emission, fluorescence lifetime, fluorescence spectrum, or scattering properties. The electromagnetic property may be predominantly in the visible electromagnetic spectrum, or in the ultra-violet spectrum, or in the infrared spectrum or in the THz spectrum or in the microwave spectrum, or in any other electromagnetic spectral range. The electromagnetic property could for example be detected by nuclear magnetic resonance, or by optical absorption detection or by Raman scattering. This list is not exhaustive and is intended to exemplify only a few possibilities for electromagnetic read outs.

Systems for detecting a change in enthalpy are also disclosed.

DETAILED DESCRIPTION

Figure 1:
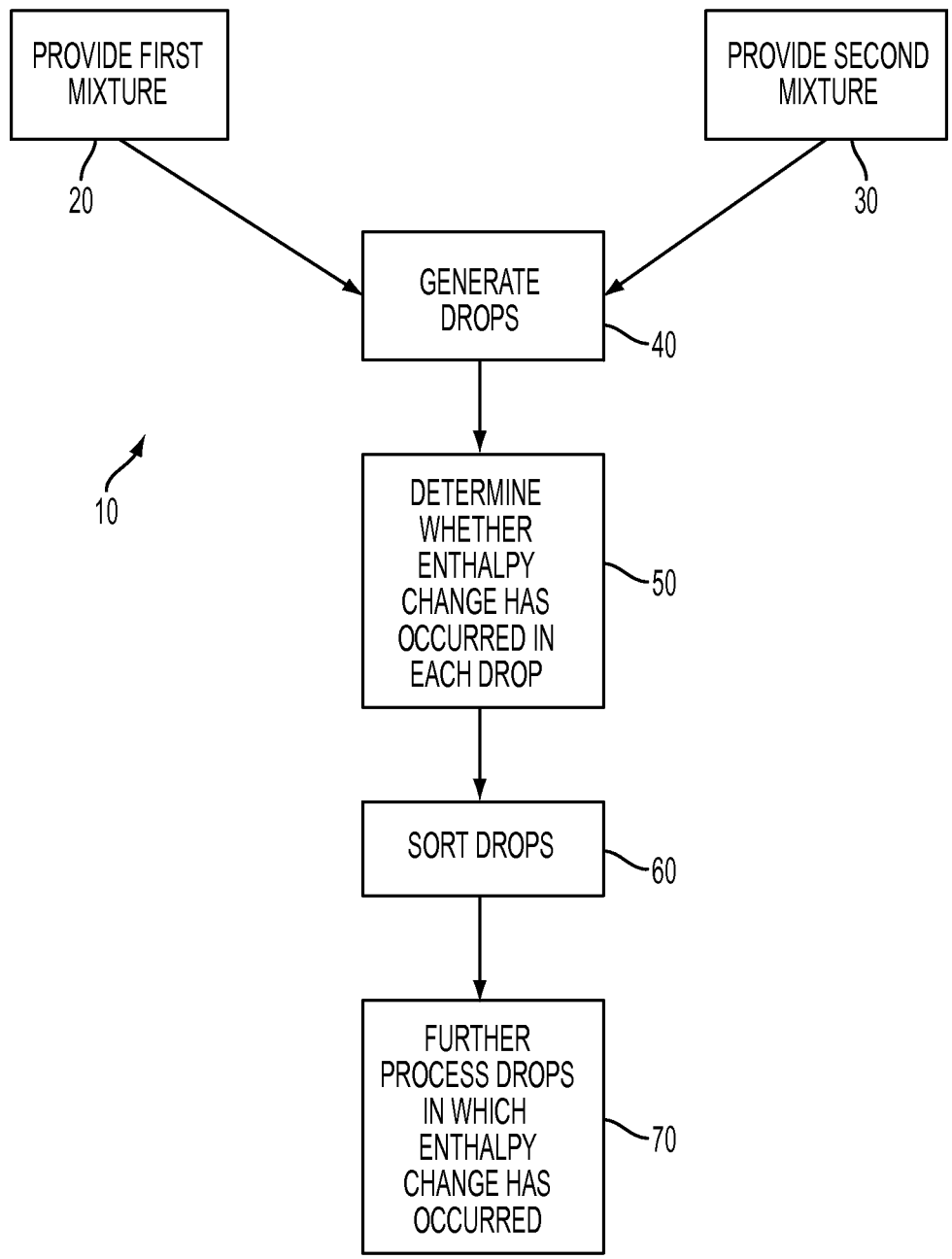
FIG. 1 is a flow chart illustrating an exemplary embodiment of a method for detecting an enthalpy change according to the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

A value modified by a term or terms, such as "about" and "substantially," may not be limited to the precise value specified. The approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

As used herein, the term "ligand" refers to an agent that binds a target molecule. This term encompasses chemical compounds of any structure, including, but not limited to, small molecules, nucleic acids and peptides. In the case in which the target molecule is a target protein, the agent may bind the target protein when the target protein is in its native conformation, or when it is partially or totally unfolded or denatured. According to the present disclosure, a ligand is not limited to an agent that binds a recognized functional region of the target protein (e.g. the active site of an enzyme), the antigen combining site of an antibody, the hormone-binding site of a receptor, a cofactor-binding site, and the like. In practicing the present method, a ligand can also be an agent that binds any surface or internal sequences or conformational domains of the target protein. Therefore, the ligands of the present disclosure encompass agents that in and of themselves may have no apparent biological function, beyond their ability to bind to the target protein in the manner described above.

As used herein, the term "test ligand" refers to an agent, comprising a compound, molecule or complex, which is being tested for its ability to bind to a target molecule. Test ligands can be virtually any agent, including without limitation metals, peptides, proteins, lipids, polysaccharides, nucleic acids, small organic molecules, and combinations thereof. Complex mixtures of substances such as natural product extracts, which may include more than one test ligand, can also be tested, and the component that binds the target molecule can be purified from the mixture in a subsequent step.

As used herein, the term "target protein" refers to a peptide, protein or protein complex for which identification of a ligand or binding partner is desired. Target proteins include without limitation peptides or proteins known or believed to be involved in the etiology of a given disease, condition or pathophysiological state, or in the regulation of physiological function. Target proteins may be derived from any living organism, such as a vertebrate, particularly a mammal and even more particularly a human. For use in the present disclosure, it is not necessary that the protein's biochemical function be specifically identified. Target proteins include without limitation receptors, enzymes, oncogene products, tumor suppressor gene products, vital proteins, and transcription factors, either in purified form or as part of a complex mixture of proteins and other compounds. Furthermore, target proteins may comprise wild type proteins, or, alternatively, mutant or variant proteins, including those with altered stability, activity, or other variant properties, or hybrid proteins to which foreign amino acid sequences, e.g. sequences that facilitate purification, have been added.

As used herein, the term "target molecule" encompasses peptides, proteins, nucleic acids, protein-nucleic acid complexes, and other receptors. The term encompasses both enzymes and proteins and nucleic acids which are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded, or triple stranded. The term encompasses a nucleic acid which is a synthetic oligonucleotide, a portion of a recombinant DNA molecule, or a portion of chromosomal DNA. The term target molecule also encompasses portions of peptides, secondary, tertiary, or quaternary structure through folding, with substituents including, but not limited to, cofactors, coenzymes, prosthetic groups, lipids, oligosaccharides, or phosphate groups. In addition, the target molecule may be part of a larger organization of molecules, For example, the target molecule may be part of a cell, a cell complex, a virus or a bacterium, or any other organism or part of an organism. The target molecule may also be connected to a particle, to a cluster of molecules, a single other molecule, or any combination of molecules.

As used herein, the term "molecule" refers to the compound, which is tested for binding affinity for the target molecule. This term encompasses chemical compounds of any structure, including, but not limited to nucleic acids and peptides. More specifically, the term "molecule" encompasses compounds in a compound or a combinatorial library. The terms "molecule" and "ligand" are synonymous.

As used herein, the term "biochemical conditions" encompasses any component, thermodynamic property, or kinetic property of a physical, chemical, or biochemical reaction. Specifically, the term refers to conditions of temperature, pressure, protein concentration, pH, ionic strength, salt concentration, time, electric current, potential difference, and concentrations of cofactor, coenzyme, oxidizing agents, reducing agents, detergents, metal ion, ligands, buffer components, co-solvents including DMSO (dimethyl sulfoxide), glycerol, and related compounds, enhancers, and inhibitors.

As used herein, the term "immiscible fluid" encompasses any liquids which do not form a homogeneous solution. Examples of immiscible fluids include, but are not limited to, an aqueous solution (water) and a fluoropolymer oil (e.g., Novec 7500, Novec 7200, Fluorinert FC-77, Fluorinert FC-40), water and silicone oil, and polar aprotic solvents (e.g., DMSO, acetonitrile) and non-polar solvents (e.g., heptane, cyclohexane).

The systems and methods of the present disclosure enable calorimetric detection of reactions in small (e.g., micron diameter (microliter to attoliter-sized)) droplets. The systems and methods are capable of identifying active compounds from a library using electromagnetic detection to ascertain whether a reaction has occurred in a droplet containing the test ligand and a target molecule. Additionally, the system can quantify the thermodynamic properties of an occurring reaction. By employing electromagnetic detection at high sampling rates (e.g., MHz sampling rates) instead of thermistor or thermocouple-based detection methods of standard calorimetry, the systems and methods can achieve orders of magnitude greater sensitivity and throughput while reducing sample consumption. The electromagnetic detection can, for example, be based on optical detection (e.g., the visible wavelength region). The optical absorption spectrum of a thermochromic material could be the electromagnetic property used to ascertain whether a reaction has occurred in a droplet and to thermodynamically quantify the reaction.

Calorimetry is used to measure enthalpic changes, including enthalpic changes arising from reactions, phase changes, changes in molecular conformation, temperature variations, and other variations of interest that may occur for a particular specimen. By measuring enthalpic changes over a series of conditions, other thermodynamic variables may be deduced. For example, measurements of enthalpy as a function of temperature reveal the heat capacity of a specimen, and titrations of reacting components can be used to deduce the binding constant and effective stoichiometry for a reaction. Calorimetry measurements are useful in a broad variety of applications, including, for example, pharmaceuticals (drug discovery, decomposition reactions, crystallization measurements), biology (cell metabolism, drug interactions, fermentation, photosynthesis), catalysts (biological, organic, or inorganic), electrochemical reactions (such as in batteries or fuel cells), and polymer synthesis and characterization, to name a few. In general, calorimetry measurements can be useful in the discovery and development of new chemicals and materials of many types, as well as in the monitoring of chemical processes.

Calorimeters can, therefore, be used to screen for substrates, cofactors, activators, and inhibitors of enzymes, including at the proteome level, and can also be used to quantify the enzymatic kinetics. Calorimeters detect the amount of heat evolved from an enzymatic reaction. The heat evolved depends on the enthalpy of the reaction, enzyme concentration, substrate concentrations, the presence of inhibitors, activators, or cofactors, values for the kinetic parameters for the reaction of interest, buffer conditions, as well as various other factors and parameters. In particular, the concentrations of the enzyme, one or more substrates, and/or regulators (e.g. agonists, inhibitors, and inverse agonists) are often a limiting factor in analyzing enzymatic reactions by detecting the enthalpy of reaction.

Isothermal titration calorimetry (ITC) is used in drug discovery and basic sciences, but the need for large samples ($\approx 0.2$ mL) and long measurement times (typically 30 min per sample) makes high-throughput measurements or measurements with limited amounts of material unfeasible.

Nanocalorimeters can overcome these limitations of conventional ITC. Thin-film thermistor-based arrays represent the state-of-the-art in nanocalorimetry. With enthalpy arrays, measurement of binding and enzymatic reactions can be used to screen compound libraries for small molecule enzyme inhibitors in sub-microliter sample volumes ($\approx 500$ nL) with much higher throughput than microcalorimeters. However, even with higher throughput (100's per day) and lower sample quantities ($\approx \frac{1}{10}^{th}$ of ITC requirements), known thermistorenthalpy arrays are insufficient to address the needs of high-throughput screening of libraries containing more than 1,000 compounds.

Instead of tagging the library or target compound with fluorescent probes, the systems and methods of the present disclosure detect reactions (e.g., binding and enzymatic reactions) via a temperature-dependent change in one or more electromagnetic properties, for example, emission wavelength, intensity, or absorption or any other change in electromagnetic property of a temperature-sensitive reporter compound which is not reactive with the library compound or the target compound. The temperature-sensitive reporter compound may be a water-soluble fluorescent reporter compound, absorption compound, scattering compound, or compound that changes its electromagnetic properties in a measurable way. The temperature-sensitive reporter compound may even be the solvent itself (e.g., the temperature-dependent shift in the Raman spectrum of water).

The photometric enthalpy detection technology enables thermodynamic characterization of binding and enzymatic reactions at the throughput of 1536-well plate assays. The combination of higher throughput and lower sample consumption allows calorimetry to be used as a primary screening method.

An electromagnetic (e.g., optical) readout of time-dependent temperature changes can be used to directly measure the heat of reactions from the response of molecular heat probes. The use of the readout and molecular heat probes allows for a reduction in the reaction volume while the use of droplets in oil (e.g., fluoropolymer oil) reduces the thermal conductivity of the surrounding environment compared to other closed-chamber microfluidic calorimeters.

In practicing the present method, the test ligand is combined with a target molecule, and the mixture is maintained under appropriate conditions and for a sufficient time to allow binding of the test ligand to the target molecule. Experimental conditions are determined empirically for each target molecule. When testing multiple test ligands, incubation conditions are usually chosen so that most ligand: target interactions would be expected to proceed to completion. In high-throughput screening applications, the test ligand is usually present in molar excess relative to the target molecule. The target molecule can be in a soluble form, or, alternatively, can be bound to a solid phase matrix. The matrix may comprise without limitation beads or other suitable solid supports.

FIG. 1 illustrates an exemplary method 10 for detecting an enthalpy change according to the present disclosure. The method 10 includes providing 20 a first mixture to a drop generator and providing 30 a second mixture to the drop generator. The first mixture contains a target molecule and may be an aqueous solution. The second mixture contains a plurality of library compounds (test ligands) and may be an aqueous solution. The method 10 further includes generating 40 drops. Each drop contains the target compound, a single molecule of one of the library compounds (test ligands), and a temperature-sensitive reporter compound. The temperature-sensitive reporter compound may be provided in the first mixture, in the second mixture, in an oil composition, and/or as a separate component.

In some embodiments, the first mixture provided via a first inlet and the second mixture is provided via a second inlet. The temperature-sensitive reporter compound may be provided via the first inlet, and/or the second inlet, and/or a third inlet.

In some embodiments, the first mixture generates a first set of drops and the second mixture generates a second set of drops. The temperature-sensitive reporter compound may be contained in the first set of drops, and/or the second set of drops, and/or a third set of drops. The reaction occurs when a drop of the first set and a drop of the second set and, if relevant, a drop of the third set merge to form a single drop due to close proximity and a reduction of surface energy upon merging. The proximity of flowing drops may be modified by features of the flow channels such as flow obstacles that affect the flow speed of drops in channels.

The drops may be generated by providing an immiscible fluid, such as fluoropolymer oil, via one or more additional inlets. In some embodiments, the additional inlets are symmetrical. Due to the immiscibility of the fluids, for example fluoropolymer oil and water, drops are generated.

The size of the drops may be controlled by adjusting the inlet sizes (e.g., diameters) and/or flow rates of the first mixture, the second mixture, and/or the oil composition. The drop size and generation method are designed such that the time for the reactants to reach each other and react is small compared with the time for thermal dissipation.

Aqueous droplet formation in oil has the advantage that a perpendicular illumination-observation direction is possible for absorption measurements. The transition of light from the higher refractive index material (oil) into the lower refractive index material (aqueous sample) allows for light detection paths that excludes incident light that did not interact with the sample droplet. Thereby, the background can be reduced.

In each individual drop, the target compound and the single molecule of the library compound may react. The reaction may be endothermic or exothermic. The temperature of the drop will change if a reaction occurs, thereby indicating that the library compound in the drop is an active compound.

Methods to generate small volume droplets are known. Microfluidic chips for generation of small droplets are commercially available from several vendors such as Raindance Technologies and Dolomite Microfluidics. The microfluidic chops may generate femtoliter droplets at a rate of 10 MHz. Since the rate-limiting step of the assay is the binding of the ligand to the target, droplet generation rates on the order to 100 kHz allows for generation of almost $10^{10}$ droplets per day.

The inclusion of a temperature-sensitive reporter compound allows the temperature change to be readily detected.

The method 10 further includes determining 50 whether an enthalpy change has occurred in each individual drop. The determination may be made by measuring one or more properties (e.g., emission wavelength) of the temperature-sensitive reporter compound. Any criteria for whether the enthalpy change has occurred can be freely defined depending on the target molecule of interest. The threshold may for example be a threshold of minimum enthalpy change or a reaction rate or any combination of desired thermodynamic quantities.

A concept similar to wavelength shifts of emission peaks could also be utilized for ratiometric color intensity measurements. Light from different fluorophroes could be directed on two different photo detectors equipped with different bandpass filters. The photocurrent of each detector is predominantly caused by emission of the associated fluorophore. The relative intensity ratio of the two channels traces the temperature dependence of the two fluorophores. For the most sensitive measurements, fluorophores show opposing temperature dependencies (i.e., the first fluorophore emits more intensely with increasing temperature while the second fluorophore decreases in intensity) can be used. For ratiometric measurements, it is insignificant if the temperature dependencies of the fluorophores influence the absorption properties of the molecule or their quantum yield. This technique is also capable of detecting fluorescence resonance energy transfer.

The method 10 may also include sorting 60 the drops based on whether the enthalpy changed has occurred.

The drops containing an active compound may be subjected to further processing 70 such as sequencing in a downstream assay (e.g., sequencing of small molecule compounds or polymers such as DNA, RNA, proteins, peptides, polysaccharides, or other natural or non-natural polymers).

In some embodiments, the first mixture contains a target molecule and may be an aqueous solution. The second mixture contains a single library compound (test ligand) and may be an aqueous solution. The method 10 further includes generating 40 drops. Each drop contains a single concentration of the target compound, a single concentration of a library compound (test ligand), and a temperature-sensitive reporter compound. The temperature-sensitive reporter compound may be provided in the first mixture, in the second mixture, in an oil composition, and/or as a separate component.

In each individual drop, the target compound and the library compound (test ligand) may react. The reaction may be endothermic or exothermic. The temperature of the drop will change if a reaction occurs, thereby indicating that the library compound in the drop is an active compound.

Figure 2:
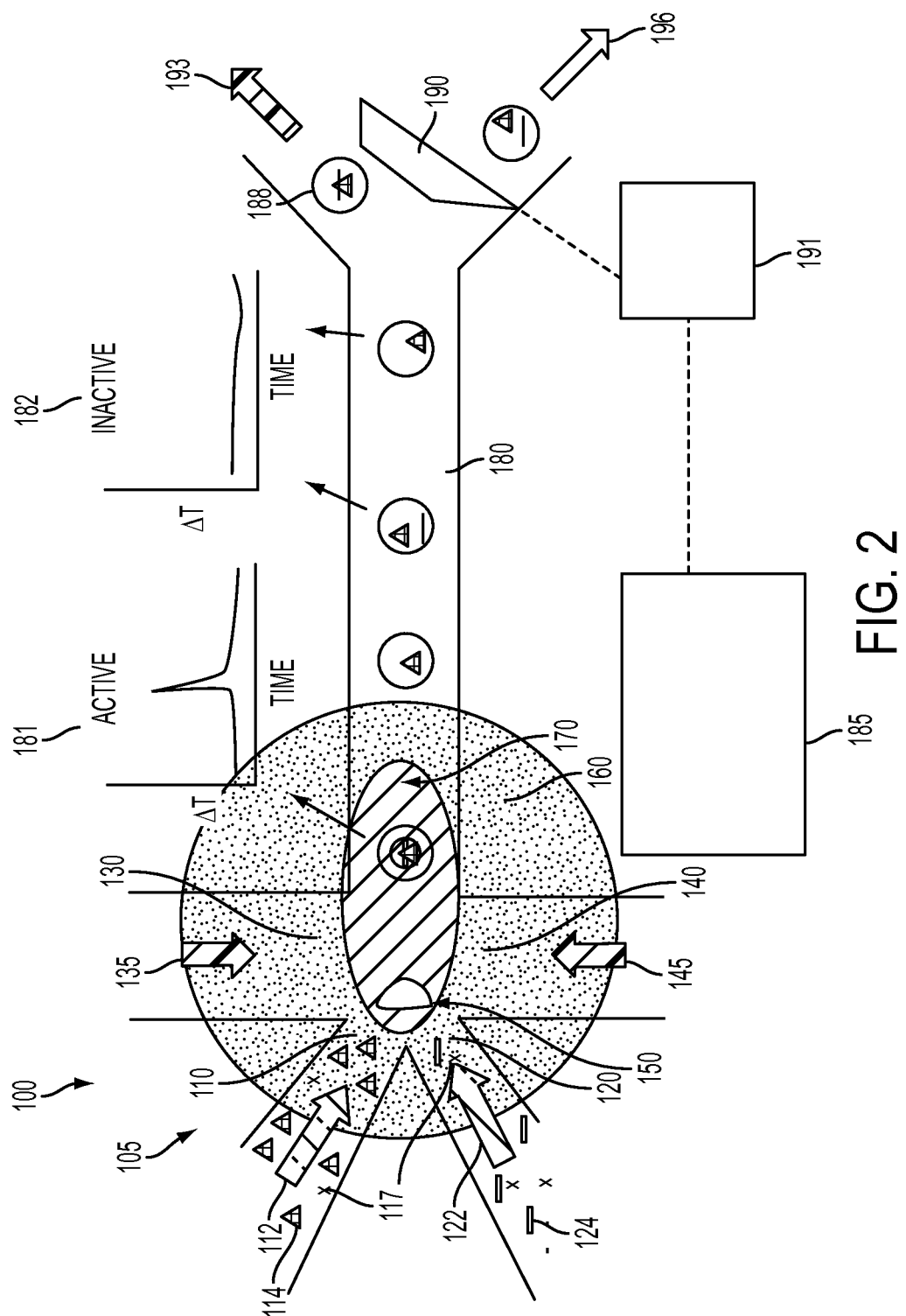
FIG. 2 is perspective view of an exemplary embodiment of a system for detecting an enthalpy change according to the present disclosure.

FIG. 2 illustrates an exemplary system 100 for detecting an enthalpy change according to the present disclosure. The system includes a drop generator 105, a sorter 190, a main pathway 180, and an electromagnetic detection unit 185. This detection unit may contain an antenna or a coil or a photomultiplier or a pin photodiode or an avalanche photodiode or a position sensitive light detector or a pyroelectric sensor or any other electromagnetic detector.

The drop generator 105 includes a first inlet 120 for receiving a first aqueous mixture 122 containing a plurality of library compounds 124, a second inlet 110 for receiving a second aqueous mixture 112 containing a target compound 114, a first oil inlet 130 for receiving a first oil composition 135, and a second oil inlet 140 for receiving a second oil composition 145. The second oil composition and the first oil composition may be the same or different. In some embodiments, one or more of the oil compositions contains the temperature-sensitive reporter compound. Some of the generated drops may contain a target compound but not a library compound.

The drop generator may be configured to generate drops having a volume of from about 65 al to about 8 nl and/or a diameter of from about 0.5 µm to about 250 µm. In some embodiments, the drop volume is from about 100 al to about 1 nl. Each aqueous drop may contain the target compound 114, a single molecule of one of the library compounds 124, and a temperature-sensitive reporter compound 117. The temperature-sensitive reporter compound may be provided via any of the above described inlets or via a separate inlet (not shown). The drops are generated in a droplet generating region 150 at the intersection of the inlets due to the immiscibility of water of the aqueous mixture and oil.

In some of the drops, a reaction occurs between the target compound 114 and the library compound 124, indicating that the library compound 124 is an active compound. The reaction briefly leads to a temperature change in an interrogation region 160. A detection unit 185 focuses on a detection region 170 within the interrogation region 160 in order to ascertain whether a reaction has occurred in each individual drop. The interrogation region 160 may consist of an illumination region in case of optical interrogation of the temperature sensitive reporter compound. The detection unit 185 may be configured to detect a temperature change based on a change in an optical spectral property (e.g., emission wavelength, absorbance wavelength, or fluorescence intensity) of the temperature-sensitive reporter compound. Graphs 181, 182 illustrate the temperature profile for drops in which a reaction has occurred (181) and has not occurred (182), respectively. Although the graphs 181, 182 are above the main pathway 180, they represent the temperature change in the detection region 170. The detection region 170 is typically smaller than the interrogation region 160. In some embodiments, one or both of the interrogation region 160 and the detection region extend into the main pathway 180 region The integral of the temperature change divided by the number of moles of reactant in the droplet yields the enthalpy change (ΔH) of the reaction when corrected for thermal dissipation, baseline temperature, and other relevant measurement conditions.

The main pathway 180 extends between the drop generator 105 and the sorter 190. The drops pass through the main pathway 180 to the sorter 190 where they are sorted based on whether or not a reaction has been detected. The sorter 190 may be controlled by a controller 191 which receives a signal from the detection unit 185 and controls the sorter 190 based on the signal. Drops 188 in which a reaction has occurred may be separated for further processing 193. The other drops may be disposed of 196 or reprocessed.

Figure 3:
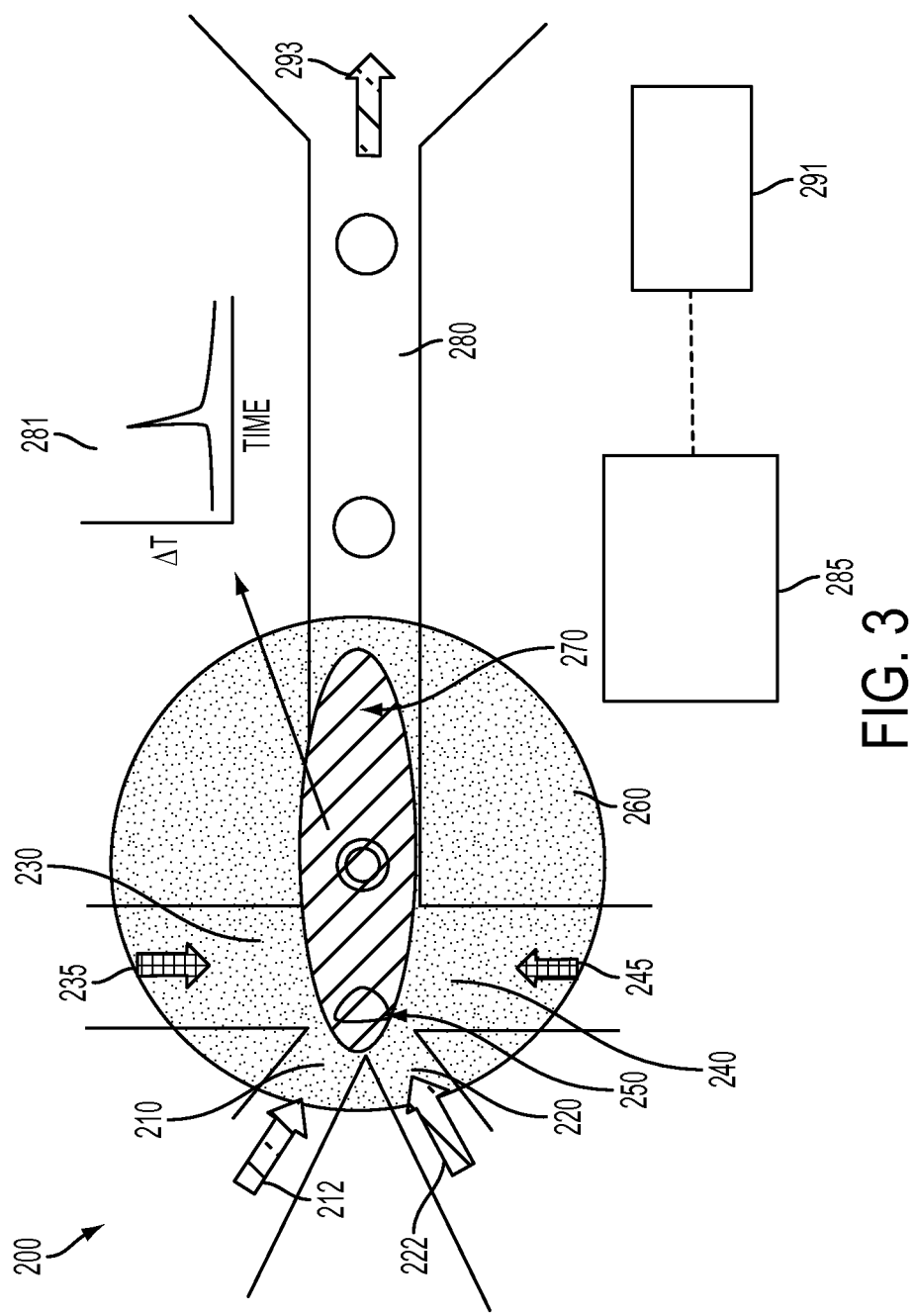
FIG. 3 is a perspective view of another exemplary embodiment of a system for detecting an enthalpy change according to the present disclosure.

FIG. 3 illustrates another exemplary system 200 for detecting an enthalpy change according to the present disclosure. The system includes a drop generator including a first inlet 220, a second inlet 210, a first oil inlet 230, and a second oil inlet 240; a main pathway 280, a detection unit 285, and a controller 291.

A ligand 212 is provided via the first inlet 210 and a target molecule 222 is provided via the second inlet. Oil is provided via the first oil inlet 230 and the second oil inlet 240. A temperature-sensitive reporter compound is provided via one or more of the first inlet 210, the second inlet 220, the first oil inlet 230, and the second oil inlet 240.

Drops are generated at a droplet generating region 250. Some of the drops may contain only one of the ligand and the target molecule. In these drops, no reaction can occur between the ligand and target molecule. Other drops contain both the ligand and the target molecule. In some of these drops, a reaction between the ligand and the target molecule can occur when the drop is in the interrogation region 260, leading to a certain amount of enthalpy change.

A detection unit 285 focuses on a detection region 270 within the interrogation region 260. The detection unit measures a property of the drop to determine an amount of enthalpy change, reaction rate and other thermodynamic properties (e.g., to ascertain whether a reaction between the ligand and target molecule has occurred). Graph 281 illustrates temperature change in a drop wherein the reaction has occurred. The drops are then transported via main pathway 280. The detection unit 285 is configured to provide a signal to the controller 291. Drops in which a reaction has occurred 293 may be recovered.

A plurality of the systems 100 and/or 200 may be stacked for screening a large number of compounds.

To aid in the identification and sorting of active from inactive compounds in complex mixtures, reactions are performed in small volumes to maximize the temperature change caused by a single reaction (e.g., a binding or catalyzed reaction). In some embodiments, the drop size and composition are selected such that a temperature change of $1.6 \times 10^{-8}$ K resulting from the binding of a single molecule is detectable.

The table below illustrates the temperature changes and thermal dissipation time constants for drop volumes used in enthalpy arrays (500 nl), common microfluidic droplet devices (2 pl), and an exemplary microfluidic device according to the present disclosure (500 al). Energy per reaction assumes that the target compound is present in excess and at a concentration significantly greater than $K_d$.

| Molecules ligand per reaction | ΔH (cal/mol) | E per rxn (cal) | ΔT (° C.) | | | Tau (sec), in fluoropolymer oil | | |
|---|---|---|---|---|---|---|---|---|
| | | | 500 nl | 2 pl | 500 al | 500 nl | 2 pl | 500 al |
| 1 | 5000 | 8.31E−21 | 1.66E−17 | 4.70E−12 | 1.66E−08 | 3.2 | 4.6E−04 | 3.3E−06 |
| 1.00E+06 | 5000 | 8.31E−15 | 1.66E−11 | 4.70E−06 | 1.66E−02 | 3.2 | 7.6E−04 | 3.3E−06 |
| 1.00E+08 | 5000 | 8.31E−13 | 1.66E−09 | 4.70E−04 | 1.66E+00 | 3.2 | 7.6E−04 | 3.3E−06 |

Single molecule reactions in droplets of 500 nl or 2 pl do not result in temperature changes large enough to be detected. However, the same reaction in a 500 al volume yields a temperature change of $1.6 \times 10^{-8}$ K. As long as detection occurs at a rate faster than tau, the heat from the binding reaction can be detected.

The drop size and generation step are designed such that the time for reactants to reach each other and react is small relative to the time for thermal response. Factors that must be considered when selecting the drop size include (1) the thermal dissipation time constant ($\tau$) for the water droplet in the oil (e.g., fluoropolymer oil) environment ($\tau$=33 ms for a 500 pl droplet in 3M Novec 7500, k=0.065 W/mK); (2) the mixing time for small molecules based on the expected diffusion length scale following droplet formation (@5 to 25 µm, $t_{mix} \approx 12$ to 280 ms for $D=10^{-9}$ m$^2$s$^{-1}$); (3) a sufficiently large steady-state $\Delta T$ for enzymatic reactions ($\approx 5$ µK, assuming $k_{cat}=10$ s$^{-1}$, $\Delta H=-5$ kcal mol$^{-1}$, [E]=10 µM); and (4) sample consumption per reaction. Although smaller (e.g., 2 pl) droplets have smaller diffusion length scales ($\approx 3$ µm, $t_{mix}=2.9$ ms), this benefit may be outweighed by a significantly shorter $\tau$ ($\approx 0.7$ ms), leading to a large attenuation ($\approx 75\%$) of the signal in binding reactions and a small steady-state $\Delta T$ ($\approx 0.16$ pK) for enzymatic reactions. Conversely, larger droplets (e.g., 500 nl droplets used in nanocalorimetry) use significantly more sample per reactions than standard HTS assays and have mixing challenges requiring micro stir bars, ultrasonic mixing, or any other means of reducing the effective diffusion length.

The table below illustrates the estimated temperature change for a binding reaction of a small-molecule ligand with a protein target and a $K_d$ of 10 µM.

The temperature-sensitive reporter compounds may be thermochromic liquid crystals. Thermochromic liquid crystals can show very large changes in optical spectra dependent upon temperature. In thermochromic liquid crystals, the spectral changes result from temperature-dependent intermolecular spacing. For example, monitoring a specific selected reflectance from a thermochromic liquid crystal surface has shown up to a 13,000% change in intensity per K in a ratiometric color measurement or a wavelength shift of hundreds of nm/K up to about 1000 nm/K. While extremely sensitive, thermochromic liquid crystal response times may restrict their use to implementations with long time constants. Faster responses are provided by thermochromic fluorescence. Prodan bound to DPPC shows an emission shift of 6 nm/K between 40° C. and 50° C. Green fluorescence protein, which shows a shift in emission wavelength by about 0.3 nm/K, is another example of a thermochromic material that could be optimized genetically/biologically. Changes in fluorescence intensity can be particularly sensitive to temperature (over 100% per degree in some cases) and have previously been used for thermography within microfluidic channels. This effect can be further improved by comparing the response of two different dyes and monitoring the change in intensity ratio between the two emission peaks, wherein the dyes are chosen such that one shows a temperature dependent fluorescence intensity change, and the other is either independent of temperature, or has a change that is opposite to the first dye.

As a non-limiting example, a thermochromic liquid crystal having a wavelength shift of about 1000 nm/K would exhibit a wavelength shift of about 16 fm when subjected to a temperature change of about $1.6 \times 10^{-8}$ K due to a single molecule reaction.

| Ligand Conc. (M) | Target Conc. (M) | $\Delta H$ (cal/mol) | Energy per reaction (J) | | T (s), fluoropolymer environment | | $\Delta T$ (K); attenuated* | |
|---|---|---|---|---|---|---|---|---|
| | | | 500 nl | 500 pl | 500 nl | 500 pl | 500 nl | 500 pl |
| 1.0E−05 | 2.0E−05 | −5000 | 6.1E−08 | 6.1E−11 | 3.2 | 0.033 | 3.1E−06 | 3.1E−06 |
| 5.0E−05 | | | 1.6E−07 | 1.6E−10 | | | 8.3E−06 | 8.3E−06 |
| 1.0E−04 | | | 1.9E−07 | 1.9E−10 | | | 9.5E−06 | 9.5E−06 |
| 5.0E−04 | | | 2.0E−07 | 2.0E−10 | | | 1.1E−05 | 1.1E−05 |

*The attenuation of temperature change based on thermal dissipation time constant relative to mixing and reaction time constants was as follows: $\Delta T = \Delta T_0$
*(1−e^(−tau/diffusion + reaction time)). For rapid mixing on length scale = ¼ drop diameter, the mixing time for 500 nl droplets is 28 seconds (250 µm) and for 500 pl droplets is 0.28 s (25 µm). Reaction time is assumed to be 5 ms.

The temperature-sensitive reporter compound 117 can be optimized in order to convert temperature changes in the drop into electromagnetic information that can be analyzed using the disclosed methods. In some embodiments, the temperature-sensitive reported compound is capable of being dispersed in an aqueous solvent, has a thermochromic optical response of greater than 5 nm/K local absorbance maximum shift, has a particle size of from about 1 to about 5 µm, and/or has no reactive groups or hydrophobic interactions with proteins so that the chance of interactions with protein or nucleic acid targets is minimized.

In order to simplify the library compound preparation and to apply the broadest materials set possible, the reporter compound 117 is dissolved into the drop to allow label-free temperature probing without modification of the reactant materials.

In some embodiments, the temperature-sensitive reporter compound is a leuco dye, a fluorophore, or a fluorescent protein. In leuco dyes, thermally induced pH changes allow detection of a reaction.

The reporter compounds may be provided as micro-sizedpolymer-encapsulated particles dispersed in water which can be readily added to the drops. The polymer encapsulant may be selected to provide a surface chemistry which reduces interactions with other components of the drop (e.g., PEGylation).

The systems and methods of the present disclosure may utilize droplet-based assays. Droplet-based assays use microfluidic devices to create small droplets of aqueous reactants in an inert carrier fluid. The benefits of these assays are no dilution of the encapsulated reactants, no interactions between reactants and solid surfaces, good thermal isolation of the droplet from surfaces, no evaporation, and compatibility with either purified macromolecules or whole cell assays. In cell-based assays, encapsulation also links phenotype of an excreted enzyme with the cell that produces it, enabling HTS for mutant enzyme production in single cells.

The microfluidic device not only serves to generate the reaction droplets; it may also include the electromagnetic detection area to monitor the response of the thermochrome to temperature changes arising from the reaction occurring in the droplet.

The electromagnetic detection unit may utilize the Palo Alto Research Center's compact optical wavelength shift detector technology where the intensity of adjacent or overlapping spectral regions is integrated and compared to determine a wavelength shift in the distribution. The integration over spectral regions can be performed by measuring the two adjacent regions with two detectors, for example, photodiodes, split photodiodes, or photomultiplier tubes (PMT). Optionally, the integration limits of a spectrum imaged on a (line-) camera can then be selected by the software settings for binning and region of interest, for flexibility of measurement adjustments. The spectral separation of light can be performed by linear variable filters or by dispersive elements (e.g., prisms, grating, etc.). For flexible measurements, stacked or multi-anode PMTs can be used on a spectrograph. The measurements may be performed at a frequency of at least about 100 Hz, up to at least about 1 MHz or even more.

The combination of a detector coating with laterally varying transmission properties and a position-sensitive photo detector (PSD) may resolve wavelength shifts significantly smaller than 10 fm. The individual photos diodes of the PSD can generate photo currents $I_1$ and $I_2$ that are amplified with a transpedance amplifier. Signal subtraction and addition are performed with an analog circuit for superior noise performance prior to sampling by the read-out computer. The center of the wavelength distribution can then be computed by $\lambda \sim (I_1-I_2)/(I_1+I_2)$. In some embodiments, the total size of the wavelength detector can closely approach that of the photo detector itself, which is beneficial for mounting and long-term stability.

The microfluidic device, aqueous compositions, and oil composition(s) may be temperature-controlled.

The detection unit is configured to detect an electromagnetic signal, for example an optical signal, from a detection region encompassing an area where the reaction may occur. The size of the detection region can be adjusted based on flow rate and the slowest expected rate of reaction ($k_{obs}$).

The optical absorption spectrum of the reporter compounds may be determined by measuring backscattered light from droplets in epi-detection configuration on an inverted microscope. For the detection and spectral analysis of the transmitted, backscattered, or fluorescence light, two selectable ports of the microscope may be utilized. Both ports can be equipped with a dichoric beam splitter to separate the optical signals from the oil and the analyte. The oil temperature reading may be used to compensate the measurement for background temperature drift during the measurement and to provide the feedback for the active oil temperature control. The oil temperature measurements may be performed with a resolution of 1 μK and 1 ms over a range of about 1 mK.

In some embodiments, one of the ports is equipped with a Czerny-Turner style spectrograph while the other is equipped with PARC wavelength shift detectors. The (magnified) detection area can be imaged onto the entrance slit of the spectrograph or on wavelength shift detectors.

The measurement system may be set up in a temperature-stabilized housing. The present systems and methods may allow measurement of temperature changes of several μK within ≈300 ms for binding reactions and over 1.5 s for enzymatic reactions. Passive insulation provides sufficient temperature stability during measurement of one reaction, while active temperature control of the oil (e.g., fluoropolymer oil) and the fluidic chip may compensate for temperature drifts larger than the measurement bandwidth (expected >1 mK) during longer periods.

The interrogation area of the microfluidic chip may include parts of the sample and oil inlet and the drop generating region in order to allow the fluids to temperature stabilize. The detection region encompasses the droplet forming region and the region in which any potential reaction would occur. The size of the detection region can be adjusted based on flow rate and the expected reaction length.

To identify background temperature fluctuations, the temperature of the oil and the temperature of the analyte droplets may be separately measured in wavelength regimes by adding reporter compounds to the oil and analyte solutions.

For optical temperature read-out, the drops may be illuminated in the drop-generating region with a probe light in order to stabilize the temperature of the materials. The illumination region is the interrogation region of the system.

In some embodiments, pulsed light sources are used to minimize the effect of droplet heating due to absorbed light. As a non-limiting example, $10^5$ drops per second may be measured, resulting in the measurement of about $10^{10}$ drops per day. Even higher throughput can be achieved through multiplexing, which is readily achievable with a planar fluidic structure (e.g., the structure depicted in FIG. 2). This approach enables HTS of compounds and sorting of droplets containing active binding or catalytic compounds. Subsequent analysis of droplets (e.g., using mass spectrometry) may be implemented after droplet sorting.

For optical temperature read-out, the illumination source may be a halogen lamp or a high-power LED.

For optical temperature read-out, the illumination light source may be external to the thermal housing to prevent unnecessary heating, particularly when the light is a high-power halogen lamp. The illumination area may have a size of from about 0.5 to about 3 mm², including from about 0.75 to about 2 mm² and about 1 mm².

The ability to measure binding reactions via calorimetry is limited by the heat of reaction. Assuming that all ligand binds to the target, the amount of heat associated with a binding reaction is:

$$Q = \Delta H_{app} \times [X] \times V,$$

wherein V is the volume of the reaction, [X] is the concentration of ligand that binds to the target ($[X]=[X]_{tot}$ under these assumptions), and $\Delta H_{app}$ is an experimentally determined molar enthalpy (usually expressed in kcal/mol or kJ/mol) for the reaction.

For enzymatic reactions, the assay is based on measuring the heat generation associated with conversion of substrate to product. The thermal power is proportional to the rate at which the enzyme converts substrate to product:

$$\frac{dQ}{dt} = \text{rate} = \frac{d[P]}{dt} \times V \times \Delta H_{app},$$

wherein V is the volume of the reaction, [P] is the molar concentration of the product, and $\Delta H_{app}$ is the experimentally determined molar enthalpy for the reaction. If sufficient substrate is provided in the reaction, the enzyme will convert it to product and this thermal power source will cause a rise (for an exothermic reaction) in the temperature of the drop over an extended period of time.

The disclosed systems and methods allow the full toolkit of synthetic chemistry to be applied in order to generate materials with a useful electromagnetic, for example optical, response for sensitive screening of reaction events. Further refinement of materials for this technique will lead to improved detection sensitivity.

The table below compares in vitro compound screening technologies. Concentrations of target and ligand assume a $K_d$ of 1 µM (for SPR, ITC, nanocalorimetry, and photometric enthalpy) and/or a ligand screening concentration of 10 µM (all methods). Photometric enthalpy throughput assumes three samples per second for a single detector. Throughput can be increased via multiplexing.

| Technique | Samples per day | Conc. of target (M) | Sample volume (L) | Target per reaction (moles) | Ligand per reaction (moles) |
|---|---|---|---|---|---|
| Labeled HTS assays (fluorescence, luminescence) | ≈200,000 (robotic multiplexing) | 1.0E−08 | 5.0E−06 | 5.0E−14 | 5.0E−11 |
| Surface plasmon resonance | 4,800 (theorhetical maximum) | Immobilized target | 5.0E−06, ligand flow | 4.2E−13 | 5.0E−11 |
| ITC | 48 | 1.0E−05 | 2.0E−04 | 2.0E−09 | 4.0E−09 |
| Nanocalorimetry | 770 | 5.0E−05 | 5.0E−07 | 2.5E−11 | 5.0E−11 |
| Photometric enthalpy | ≈260,000 | 2.0E−05 | 5.0E−13 | 1.0E−17 | 2.0E−17 |

The label-free, solution-based HTS systems and methods of the present disclosure facilitate the identification of compounds acting specifically on intended targets.

Non-limiting examples of applications for the systems and methods of the present disclosure include targeted cancer therapeutics. Targeted cancer therapeutics refers to cancer drugs designed to interfere with a specific molecular target which has a role in tumor growth or progression. Histone deacetylases (HDACs) have emerged as promising cancer therapeutic targets. Two histone deacetylase inhibitors (vorinostate and romidepsin) have been approved for cancer therapy and others are undergoing clinical trials. However, these inhibitors have shown a lack of specificity, so identifying inhibitors with higher specificity is important to reduce the side-effects associated with these compounds. The systems and methods of the present disclosure allow such identification.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A method for performing calorimetry comprising:
   providing a first mixture comprising a first portion of a first fluid and a ligand to a drop generator;
   providing a second mixture comprising a second portion of the first fluid and a target molecule to the drop generator;
   generating a drop in a second fluid, wherein the first fluid and the second fluid are immiscible, the drop comprising the target molecule, a temperature-sensitive reporter compound, and the ligand; and
   measuring a temperature of the drop over time by measuring a property of the temperature-sensitive reporter compound to perform calorimetry.

2. The method of claim 1, further comprising:
   generating an electromagnetic readout or an optical readout of drop temperature.

3. The method of claim 1, wherein either the first mixture, the second mixture, or both the first and second mixtures comprises the temperature-sensitive reporter compound.

4. The method of claim 1, wherein the second fluid comprises the temperature-sensitive reporter compound.

5. The method of claim 1, wherein the temperature is measured based on an emission wavelength range or an absorption wavelength range of the temperature-sensitive reporter compound.

6. The method of claim 1, wherein the drop has a volume of less than about 10 microliters and greater than about 50 attoliters.

7. The method of claim 1, wherein the target molecule is selected from the group consisting of proteins, enzymes, DNA, RNA, peptides, oligosaccharides, cells, viruses, bacteria, dormant organisms, and microorganisms.

8. The method of claim 1, wherein the ligand is selected from the group consisting of proteins, DNA, RNA, peptides, oligosaccharides, enzyme substrates, enzyme cofactors, and enzyme inhibitors.

9. The method of claim 1, wherein a concentration of the target molecule ranges from a single molecule per drop to 1 mole per liter.

10. The method of claim 1, wherein a concentration of the ligand ranges from a single molecule per drop to 1 mole per liter.

11. The method of claim 1, wherein the first fluid is aqueous and wherein the second fluid is a fluoropolymer oil.

12. The method of claim 1, wherein the temperature-sensitive reporter compound is a thermochromic liquid crystal.

13. The method of claim 1, further comprising:
    recovering the drop if a predefined amount of enthalpy change has occurred.

14. The method of claim 1, further comprising:
    calibrating the temperature measurement using a known ligand and a known target molecule concentration to cause a known enthalpy change.

15. A process comprising:
providing a first mixture comprising a first portion of a first fluid and a plurality of library compounds to a drop generator;
providing a second mixture comprising a second portion of the first fluid and a target compound to the drop generator;
continuously generating drops, each drop comprising the target compound, a temperature-sensitive reporter compound, and a single molecule of one library compound;
measuring a property of the temperature-sensitive reporter compound in each drop to perform calorimetry; and
sorting each drop based on at least one predetermined thermodynamic variable.

16. The process of claim 15, wherein the property is an emission wavelength range or an absorption wavelength range.

17. A system for performing calorimetry comprising:
a drop generator comprising:
   a first inlet for receiving a first mixture comprising a first portion of a first fluid and ligands;
   a second inlet for receiving a second mixture comprising a second portion of the first fluid and a target compound;
   one or more additional inlets for receiving a second fluid, the first and second fluid being immiscible;
   a droplet generating region at the intersection of the first inlet, the second inlet, and the one or more additional inlets; and
   an outlet;
   wherein the drop generator is configured to generate drops comprising the target compound, a temperature-sensitive reporter compound, and a ligand;
a main pathway between the outlet of the drop generator and a system outlet, the main pathway comprising an interrogation region; and
a detection unit configured to detect a temperature-dependent property of the temperature-sensitive reporter compound as each drop passes through the interrogation region.

18. The system of claim 17, further comprising:
a sorter downstream of the interrogation region configured to sort the drops based on at least one predetermined thermodynamic variable.

19. The system of claim 17, wherein the temperature-dependent property is an emission wavelength range or an absorption wavelength range.

20. The system of claim 17, wherein the detection unit is an optical detection unit.

* * * * *